(12) United States Patent
Kovacs

(10) Patent No.: US 10,635,782 B2
(45) Date of Patent: Apr. 28, 2020

(54) PHYSICAL EXAMINATION METHOD AND APPARATUS

(71) Applicant: Gregory T. Kovacs, Palo Alto, CA (US)

(72) Inventor: Gregory T. Kovacs, Palo Alto, CA (US)

( * ) Notice: Subject to any disclaimer, the term of this patent is extended or adjusted under 35 U.S.C. 154(b) by 241 days.

(21) Appl. No.: 15/456,493

(22) Filed: Mar. 11, 2017

(65) Prior Publication Data
US 2017/0185737 A1 Jun. 29, 2017

Related U.S. Application Data

(63) Continuation of application No. PCT/US2015/049809, filed on Sep. 11, 2015.
(Continued)

(51) Int. Cl.
*A61B 5/0205* (2006.01)
*G06F 19/00* (2018.01)
(Continued)

(52) U.S. Cl.
CPC .......... *G06F 19/3418* (2013.01); *A61B 5/002* (2013.01); *A61B 5/0006* (2013.01); *A61B 5/0095* (2013.01); *A61B 5/024* (2013.01); *A61B 5/0205* (2013.01); *A61B 5/0245* (2013.01); *A61B 5/02416* (2013.01); *A61B 5/02438* (2013.01); *A61B 5/0404* (2013.01); *A61B 5/04012* (2013.01); *A61B 5/04023* (2013.01); *A61B 5/0476* (2013.01);
(Continued)

(58) Field of Classification Search
CPC . A61B 5/0205; A61B 5/02438; A61B 5/0245; G06F 19/3418

USPC .......................................................... 600/301
See application file for complete search history.

(56) References Cited

U.S. PATENT DOCUMENTS 4,712,562 A 12/1987 Ohayon et al.
5,339,821 A 8/1994 Fujimoto
(Continued)

FOREIGN PATENT DOCUMENTS

EP 2248461 A2 11/2010

OTHER PUBLICATIONS

Lee, Y.-S. et al., Recognizing multi-modal sensor signals using evolutionary learning of dynamic Bayesian networks, Pattern Analysis and Applications, vol. 17, Issue 4 (Sep. 26, 2012).

*Primary Examiner* — Alyssa M Alter
(74) *Attorney, Agent, or Firm* — Crawford Maunu PLLC

(57) ABSTRACT

Certain exemplary aspects of the present disclosure are directed towards methods and apparatuses for conducting physical examinations of a human. Optionally, such embodiments permit for remote examination of a patient, for example, the patient's heart or lung region. In such embodiments, a user operates a remote physical examination sensor, while a remote examination computer and/or remote medical personnel reviews/analyzes medical data received from the remote physical examination sensor to diagnose the condition of the user. The remote physical examination instrument may be equipped with a plurality of skin-compatible electrodes on a remote examination sensor connected to the user's chest, as well as one or more electrodes on the top cover or sides of the remote examination sensor connecting to the user's hand and providing medical data to the remote examination computer.

36 Claims, 5 Drawing Sheets

Related U.S. Application Data

(60) Provisional application No. 62/049,868, filed on Sep. 12, 2014.

(51) Int. Cl.

| | | |
|---|---|---|
| *A61B 7/04* | (2006.01) | |
| *A61B 5/024* | (2006.01) | |
| *A61B 5/0408* | (2006.01) | |
| *A61B 5/0476* | (2006.01) | |
| *A61B 5/053* | (2006.01) | |
| *A61B 5/0404* | (2006.01) | |
| *A61B 5/00* | (2006.01) | |
| *G16H 10/60* | (2018.01) | |
| *A61B 5/0245* | (2006.01) | |
| *A61B 5/04* | (2006.01) | |
| *A61B 5/0402* | (2006.01) | |
| *G06Q 50/24* | (2012.01) | |
| *G06Q 50/22* | (2018.01) | |

(52) U.S. Cl.
CPC ........ *A61B 5/04085* (2013.01); *A61B 5/0535* (2013.01); *A61B 7/04* (2013.01); *G06Q 50/24* (2013.01); *G16H 10/60* (2018.01); *A61B 5/0002* (2013.01); *A61B 5/6823* (2013.01); *A61B 5/6886* (2013.01); *G06F 19/34* (2013.01); *G06Q 50/22* (2013.01)

(56) References Cited

U.S. PATENT DOCUMENTS

| | | | |
|---|---|---|---|
| 6,726,638 | B2 | 4/2004 | Ombrellaro |
| 8,630,867 | B2 | 1/2014 | Yoo |
| 2002/0111777 | A1* | 8/2002 | David ............... A61B 5/04085 702/189 |
| 2004/0230458 | A1 | 11/2004 | Takayama et al. |
| 2009/0240297 | A1* | 9/2009 | Shavit ..................... A61N 1/39 607/5 |
| 2012/0085905 | A1 | 4/2012 | Centen et al. |
| 2014/0163349 | A1* | 6/2014 | Amitai ................... G16H 40/67 600/393 |
| 2014/0243612 | A1 | 8/2014 | Li et al. |

* cited by examiner

US 10,635,782 B2

PHYSICAL EXAMINATION METHOD AND APPARATUS

OVERVIEW

Various aspects of the present disclosure are directed to physical examination sensors useful in connection with remote physical examination methods, systems, and apparatuses, and more particularly to cardiovascular examinations of the heart and lungs. Specific aspects of the present disclosure are more specifically directed to such sensors used for performing remote physical examinations, for example, where a user/patient is located remote from the examination machine or physician acting on data provided by the sensor configured to perform cardiovascular examinations of the heart and lungs. Clinic-quality examinations involving sensors are difficult to implement remotely, and may provide inconclusive results due to improper placement of sensor leads on the patient and/or provide false readings that result in a misdiagnosis. These and other matters have presented challenges to remote physical examinations, for a variety of applications including auscultation (e.g., using acoustic information via stethoscope), and electrocardiogram (ECG) examinations.

Various example embodiments are directed to apparatuses, systems, and methods of use that address these challenges.

Aspects of the present disclosure are believed to be applicable to a variety of different types of apparatuses, systems and methods involving sensing of physiological characteristics, as may be implemented via remote examinations. For example, aspects of the present disclosure allow for a user (e.g., patient) to operate a remote physical examination sensor, while a remote examination computer or remote medical person reviews/analyzes medical data received from the remote physical examination sensor to diagnose a condition of the user.

In some embodiments, a physical examination instrument is equipped with a plurality of skin-compatible electrodes on a remote examination sensor in contact with the user's chest, as well as one or more electrodes on the top cover or sides of the remote examination sensor connecting to the user's hand.

Other embodiments are directed toward methods in which a user is guided, remotely by a health care provider, through an examination. In some embodiments, the examination process is automated by computer circuitry, with instructions being provided by the computer circuitry and the resulting data from the examination being stored, either remotely or on a health care provider computer system. When a healthcare provider is available, the data from the examination can be gathered from the storage location for viewing/analysis.

In certain other embodiments, a physical examination instrument is configured to obtain ECG-type signals which are then mathematically processed to generate an output signal representative of one or more standard ECG leads (e.g., standard 12-lead, or partial). These ECG signals may be obtained via ECG electrodes, integrated with the physical examination instrument and positioned at different locations on the thorax and/or via additional electrodes separate from the instrument. For instance, variations in heart rate over time (e.g., due to breathing or relaxing) can be accounted for, and positioning of the apparatus 300 (e.g., as sensed via orientation sensors), can be used in generating the output signal.

DESCRIPTION OF THE FIGURES

Various example embodiments may be more completely understood in consideration of the following detailed description in connection with the accompanying drawings, in which.

Figure 1:
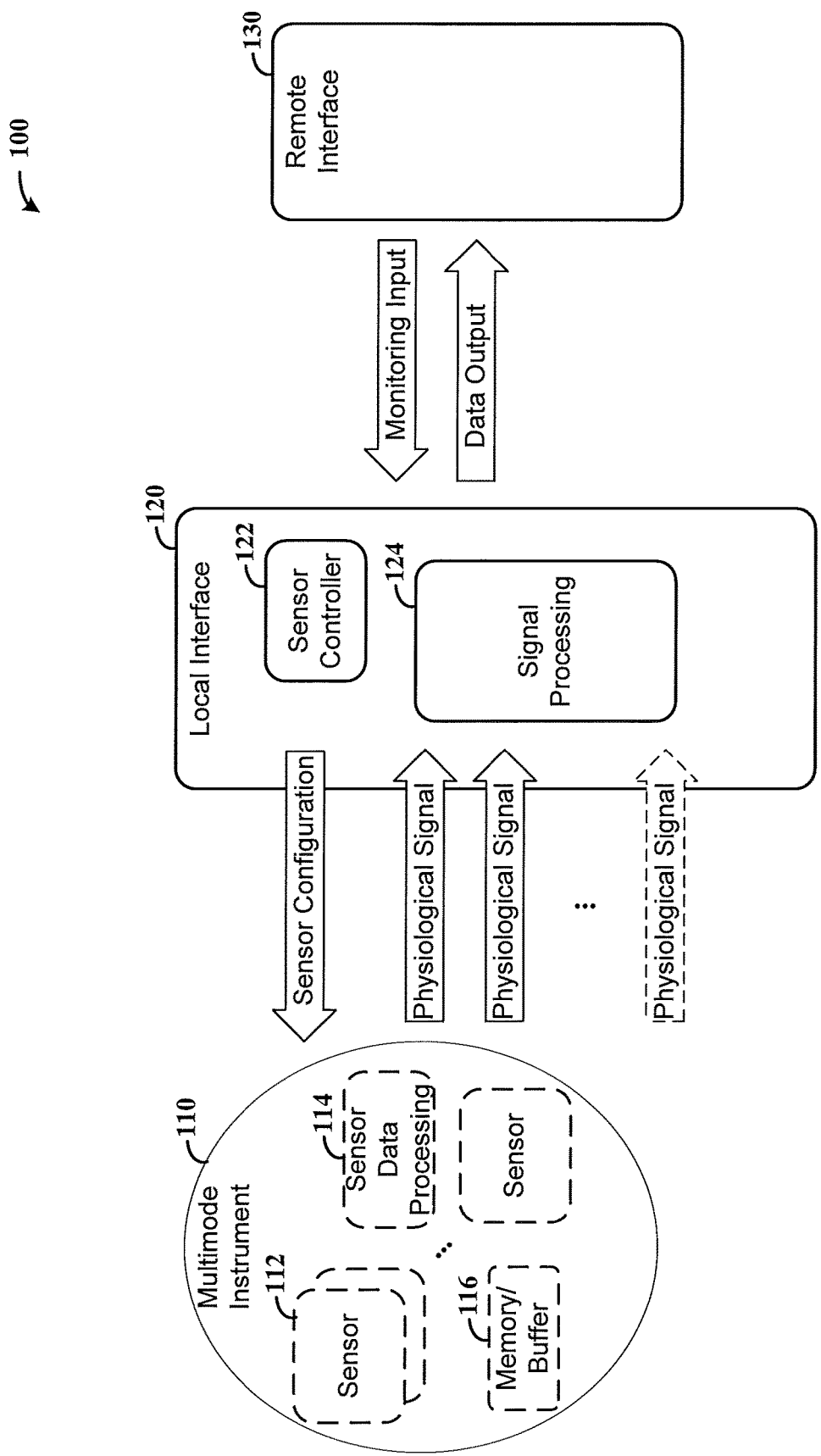
FIG. 1 shows a block diagram of an exemplary remote examination instrument apparatus, consistent with various aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of different types of apparatuses, systems and methods involving sensing of physiological characteristics, as may be implemented via remote examinations. While not necessarily so limited, various aspects of the invention may be appreciated through a discussion of examples in this regard.

Aspects of the present disclosure allow for a user (e.g., patient) to operate a remote physical examination sensor, while a remote examination computer or remote medical person reviews/analyzes medical data received from the remote physical examination sensor to diagnose the condition of the user. In some specific embodiments, a user is visually or otherwise guided through hand-placement of the remote physical examination sensor, such as on the user's chest, to collect data as would be obtained during an in-person cardiovascular examination such as auscultation (stethoscope), ECG and other cardiovascular examinations that are conducted by a licensed physician or qualified medical personnel.

In some embodiments, a remote physical examination instrument is equipped with a plurality of skin-compatible electrodes (compliant and/or spring loaded) on a rim along the perimeter of the remote examination sensor in contact with the user's chest, as well as one or more electrodes on the top cover or sides of the remote examination sensor connecting to the user's hand. The instrument may also include one or more acoustic sensors and vibration sensors, among other optional sensors for procuring further measurements, and/or position sensors (e.g., a camera, a magnetic sensor, an inertial measurement unit, and/or beacons). In some embodiments, optical beacon(s) may be mounted to the top cover of the sensor on the exterior of the instrument, the light emitted from the beacons being received and processed by a camera/light sensor circuit a short distance from the patient and communicated to the remote examination computer to determine current positioning of the sensor relative to the patient and to determine any corrective measures needed to reposition the sensor to the proper location on the patient for optimal sensor measurements. In some embodiments, an inertial measurement unit (IMU), which may be in an integrated-circuit form, is included such that the instrument can determine its tilt and rotation relative to the Earth's gravitational force. A magnetic compass sensor may also be included for additional position information or to sense a magnet deliberately located in the area, for example on the local screen used to guide the user/patient.

Other embodiments are directed towards methods in which a user is guided, remotely by a health care provider (e.g., doctor, nurse, or software entity), through a remote cardiology examination, for example. The ability for patients to conduct such remote examinations, located potentially hundreds of miles from their health care provider, could prevent an otherwise unnecessary journey to a medical clinic which may be unreachable by the user due to socioeconomic, military, climate or other impeding forces. In some embodiments, the examination process is automated by computer circuitry (either by a remote examination computer or a physician computer system communicatively coupled thereto via a cellular or other communication channel), with instructions being provided by such computer circuitry and the resulting data from the examination being stored, either remotely or on the physician computer system. When a healthcare provider is available, the data from the examination can be gathered from the storage location for viewing/analysis.

In certain embodiments, an examination system includes a remote physical examination instrument, a camera that faces a user during his or her examination, processor circuitry (e.g., an examination computer), as well as a monitor. The remote physical examination sensor is outfitted with one or more light emitting diodes (LEDs) attached to a rim and/or a top cover thereof as well as an IMU to provide additional information such as tilt and rotation. The monitor displays an image of the patient, obtained using the camera. A marker, such as a blinking red dot, is provided at a location for measurement determined by the processor circuitry, as may be determined based on an algorithm or via selection by a remote health care provider. The patient is provided with visual confirmation of proper remote physical examination sensor position via the monitor. In certain specific embodiments, successful positioning of the instrument is relayed to the patient via a change of color blinking on the on-screen marker (e.g., from red to green), an audible tone or a vibration from the instrument. Further examinations or multiple measurements for an examination are completed by a similar methodology in various embodiments, involving location selection and patient relocation of the sensor. Verbal and/or image feedback from the remote healthcare provider (or processor circuitry) drives patient actions, such as movement of the sensor, coughing, Valsalva maneuver, taking breaths, holding breaths and exhaling.

Further aspects of the present disclosure are directed to selecting optimal electrodes on the remote physical examination instrument for a selected physical examination or mode of examination. For example, for an ECG examination, electrodes are to be selected from electrodes on the rim of the instrument based in part on the location and orientation of the sensor as reported to a processing circuitry by a camera. For instance, sensor alignment with the main cardiac vector or cardinal ECG leads can be achieved by selecting a subset of sensors that provide such an alignment, such as shown in the Appendix of the underlying Provisional Application No. 62/049,868 (the "Provisional", which is fully incorporated by reference and to which benefit is claimed for common subject matter). This patent application is also a continuation of related to International Application No. PCT/US2015/049809, filed Sep. 11, 2015, which is also incorporated by reference in its entirety for any purpose whatsoever.

ECG measurements could also be made relative to an additional electrode on the top of the sensor which contacts a finger or palm of the patient's hand, allowing for a "limb" lead referenced ECG relative to any of the plurality of sensors on the rim of the sensor. Alternatively, electrodes on the sensor can be provided to touch the thumb and index finger, for example, for a "pinch" grip. In either palm or "pinch" locations, multiple electrodes can be used to measure the local tissue impedance variations or optical variations via photoplethysmography (PPG) with each pulse, providing another method of measuring heart rate or pulse arrival time (PAT). From the PAT measurement, pulse wave velocity can be estimated, as well as blood pressure.

Various embodiments are directed to simulating or otherwise operating to provide sensing characteristics of standard ECG leads, such as precordial leads, with a multimodal sensor as discussed herein. Such embodiments provide an approximation of signals from the standard ECG leads, based on the position of the instrument, and the signals received from electrodes on the instrument relative to the limb/hand lead. In certain embodiments, an important operating principle involves assembling ECG signals measured by the instrument at various locations together, and mathematically synthesizing the signals into equivalent standard electrocardiogram leads. This approach is facilitated via relative stability of the underlying physiology over the course of the time needed to undergo remote diagnosis, and with corrections (e.g., correction algorithms for variations in heart rate over the measurement period), estimates of the standard ECG lead signals can derived. This can be beneficial in the case of remote physical examination, and can mitigate a need to attach numerous discrete electrodes and a cumbersome set of wires (e.g., to the patient's chest, with attendant large potential for erroneous placements). In one such embodiment, acoustic (auscultatory) signals are also obtained via a microphone within a dome of the instrument facing the patient. In such embodiments, such multimodal operation permits for simultaneity of data capture in which multiple modes are dynamically interleaved (e.g., temporally) such that they are in effect parallel and time-synchronous. This allows for heretofore very difficult modes of operation such as simultaneous capture of synchronized ECG and heart sound information, which allows analysis of detailed timings, valve functions, and the like. In another embodiment, a patient is guided through hand-placement of a remote physical examination instrument on his or her chest (among other locations) to provide quality data as would be obtained via auscultation (stethoscope), ECG and/or other measurements. This guiding may be effected by using one or more of visual, vibration or acoustic cues, and other communication. In one such embodiment a camera-equipped interface such as a tablet, smartphone or laptop (functioning as the remote examination computer) displays a view of the patient's chest and if desired, an image of the remote physician (or written/visual instructions, such as visual cues on the displayed image of the patient's chest). The interface provides patient guidance as to placing the instrument, as well as any other instructions for completing the examination.

In a particular embodiment, a multimodal instrument includes a circular array of electrodes around a chest-contacting perimeter of the instrument and an electrode on the backside of the instrument that contacts a palm of a patient applying the instrument with his or her hand. ECG waveforms are recorded using a combination of two or more of the perimeter electrodes (or, e.g., one or more perimeter electrodes relative to the palm or "pinch" electrodes on the surfaces of the multimodal instrument), which may be selected based upon positioning of the multimodal instrument. Signals captured by the electrodes are used to mathematically reconstruct signals corresponding to ECG leads as would be coupled to different locations on the patient. In this context, the term "lead" is not necessarily limited to a physical wire, but may include a standard "lead" or trace as used in the practice of cardiology and general medicine. Electrode signals may be recorded in parallel and stored electronically, with the mathematical reconstruction of standard and non-standard "lead" signals being carried out later or in real-time, for example, using locally-situated circuitry (or a local interface circuit) such as by a local computer or using remotely-situated circuitry such as the remote physician's computer. For instance, communication bandwidth may be saved by performing computations at the patient's location or alternatively, a remote location such as the care-provider's remotely located office. The skilled artisan would appreciate that the local interface circuit (situated locally or remotely) could also be implemented using a smart phone, tablet, set-top box, gaming console, etc., for performing display functions of processed data for the user or medical personnel and/or also for performing computations on raw or less-processed data provided or derived from the leads of the examination instrument. Various embodiments employ additional sensors such as acoustic, accelerometric photoplethysmographic, impedance, or others incorporated into the multimodal instrument in various combinations, allowing the instrument to examine other physical characteristics of the patient more thoroughly and to extend the examination beyond the cardiovascular system.

In another embodiment, a user/patient holds a remote examination instrument including a hollow puck or dome-shape and a ring of electrodes located at a chest-contacting base of the instrument, a palm electrode on its apex and an acoustic sensor (e.g., microphone) inside the hollow dome of the instrument (see apical diagram in Provisional Appendix). In other implementations, a rubber-tipped probe that physically touches the body is implemented in lieu of or in addition to such a "cup", hollow space, or contact-type acoustic sensor, with a sensor such as a microphone. Other sensors are, as mentioned above, included for particular embodiments providing further examination functionality. During the examination, the patient is provided with a self-image via a wireless communication feed from a camera facing the patient. In some embodiments the camera is hardwired with a local interface (or local interface circuit) such as an examination computer or tablet with an onboard camera. On an image of the patient's chest, a marker such as a blinking red dot is provided at a location for measurement desired by a remote health care provider. As the user moves the instrument, location and orientation of the remote examination instrument is calculated based on LEDs mounted on the instrument, which provide identifiable blinking patterns, colors or wavelengths, which are then detected by the camera and interpreted by software to estimate location on the patient's chest. In other embodiments, positional feedback is provided via a remote physician. At each location, the instrument is held in place for several seconds to obtain valid data, at which time a remotely cued repositioning cycle is repeated until sufficient data is collected. In some embodiments, an additional camera(s) could be used to provide side views if desired for better three-dimensional (3D) positioning accuracy.

In another embodiment, a remote physical examination system is completely self-contained in a remote physical instrument. The remote physical examination instrument includes various sensors for obtaining readings from a patient, location and processing circuits for determining the location/orientation of the instrument relative to the patient's body, diagnosis circuits and indicators that instruct the patient to relocate the instrument relative to his or her body. In some embodiments, the instrument is outfitted with at least one of a gyroscope, accelerometer, camera and/or other instruments that provide inputs useful for determining the location of the instrument relative to the patient's body. In yet further embodiments, the instrument includes communication circuits that communicate with a remote medical practitioner, such as for providing detected data or relaying instructions to the patient.

In further more specific embodiments, to help facilitate orientation detection of the remote examination instrument, a miniature gyroscope/accelerometer combination (e.g., providing six axes of feedback), such as an inertial measurement unit (IMU), is included in the instrument. The IMU is used to determine orientation (e.g., tilt and rotation) of the instrument and which of the respective electrodes are best positioned for collecting cardiac signals.

In certain embodiments, a remote examination instrument is used for ECG recording by positioning for sensing such signals from a user's heart, and is further used for auscultation recording of the heart and lungs by positioning in respective locations on the user's back. After completing the recording cycles at each position, the recorded signals at each body location are combined computationally using approaches such as feature-based alignment, ensemble averaging and interpolation. Corresponding ECG lead signals can be derived relative to the cardiac axis.

In various example embodiments, communication between a multimodal instrument and a local interface is via one or more of a cabled connection (e.g., USB) or wireless connection such as Bluetooth or WiFi. With higher bandwidth connections between the remote examination computer and a physician's computer station, two-way video may be used to interact with the patient. With intermediate bandwidths, reduced frame rates of visual feedback to the patient could be provided, with voice or text feedback to them from the remote physician. For very low bandwidths, the video feedback for positioning could be essentially local, with a very low frame rate transmitted to a remote physician's computer in which a next target location can be indicated with, for example, a mouse click that provides a "target dot" or other indicator that is transmitted to and overlaid upon a patient-end image of his or her body on a display.

In some embodiments, an instrument as described herein includes a microcontroller that is programmed, such as via a Micro USB 2.0 port that is also used to charge a battery in the instrument. Upon activation of the instrument, the microcontroller initiates a wireless communication channel, such as via a Bluetooth transceiver (utilizing BLE 4.0 communication protocol, for example), to a local interface such as a laptop, tablet or cell phone and a camera. The microcontroller initiates LED drivers that power the LEDs on the instrument. The camera transmits images of the instrument orientation (as indicated by the LED lights) to the local interface, which initiates an algorithm to determine the orientation and position of the instrument relative to the target position of the instrument on the patient's body. If the instrument is not properly oriented, the local interface alerts the patient that further movement is needed, such as via visual, audible or physical indications such as vibration.

When the instrument is located and oriented properly relative to the patient, the local interface alerts the user of the proper orientation (e.g., momentarily operating vibration motors in the instrument or emitting a pleasant audio tone) and transmits a signal to the instrument to initiate a sensing protocol as discussed herein. Various sensing sub-circuits for detecting particular types of physiological characteristics are operated in the instrument, according to the local interface. The instrument then transmits signals indicative of a condition of a patient being examined, to the local interface.

In some implementations, the microcontroller processes instrument data, prior to communicating to the local interface, to reduce the transmitted data volume or to determine a preliminary diagnosis of the patient. Depending upon the preliminary diagnosis, the signals may or may not be sent to the local interface circuit. Further, the local interface circuit may similarly selectively diagnose conditions and send related data to a remote location for further processing or analysis (e.g., to a medical professional).

Another example embodiment is directed to a method as follows. A multimodal instrument is placed against the body of a user and used to capture a plurality of different types of physiological signals from the user. Each type of physiological signal is captured during operation in one of the respective modes, with each mode corresponding to at least one of a plurality of physiological characteristics. For instance, certain modes may involve capturing different physiological signals in parallel (or with overlapping capture), or capturing a single physiological signal. In this context, multiple characteristics of the user may be captured at once, such as by capturing audio (e.g., auscultatory), PPG, and ECG signals at the same time.

Accordingly, a local interface circuit is used with the multimodal instrument to operate the instrument in one of the modes for capturing one or more of physiological signals, and to collect and record data corresponding to one or more characteristics of the user corresponding to the mode being used. For instance, two or more of electrical characteristics, optical characteristics, chemical characteristics and mechanical characteristics may be captured in this regard. Results that characterize the collected data can then be transmitted over a communications network, such as by transmission over wired or wireless connections that may include one or more of USB, BlueTooth, WiFi, cellular, infrared and other communication links. The data can then be analyzed remotely (e.g., by a medical professional), with related feedback and control optionally provided to the user via the interface.

In some embodiments involving the recording of different types of physiological signals from the multimodal instrument in parallel, a signal that characterizes a physiological characteristic is mathematically constructed based on the different types of recorded physiological signals. The constructed signal is then transmitted via the communications network. For example, if the ECG signal is strong, it can be used as a trigger for processing of other signals, such as to synchronize ensemble averaging of a lower signal-to-noise ratio signal (e.g., impedance plethysmography).

In certain embodiments, the multimodal instrument is a handheld instrument and the user places the handheld instrument against his or her body by grasping the handheld instrument. This approach may involve, for example, capture of signals from the user's body as well as another signal (e.g., a reference signal) from the user's hand. Such reference sensors may include, for example, one or more of a recording electrode, PPG sensor or impedance-based pulse sensor. Examination of the user is thus remotely directed via instructions provided in regard to placement, via the interface, with the user placing the multimodal instrument against his or her body. This approach may, for example, involve a combination of providing video feedback of the user and instrument, and related feedback that directs the user where to place the multimodal instrument. Placement of the multimodal instrument may, for example, be provided by a remote care provider, an avatar (e.g., via video or audio with snapshot images), printed instructions with diagrams (as in Provisional Appendix) or other software interface, and may use tactile (vibratory) feedback, audio cues, visual cues or other interactive features to guide placement of the multimodal instrument to target locations.

In certain embodiments in which the multimodal instrument includes two or more sensors that sense different types of user characteristics, the local interface circuit controls the instrument for selectively operating one or both of the first and second sensors based on a particular one of the modes selected. As such, various modes may involve one, two or more sensors (e.g., with related signals being captured in parallel). Such approaches may involve operating the multimodal instrument according to two or more different types of sensing protocols for sensing different physiological characteristics. Such protocols may be stored and executed in the local interface circuit for controlling the operation of the instrument. For instance, the local interface circuit may process the collected data based on an algorithm associated with the physiological characteristics, and transmit the processed data over the communications network.

In a particular embodiment involving a reference instrument (e.g., ballistocardiogram scale, BP cuff, clip-on photoplethysmogram), a separate remote instrument (e.g., a clip-on toe/finger sensor or another of the above-exemplified instruments) is placed against the body of the user and used to provide a reference output signal that can be used by the local interface circuit, relative to one or more signals obtained by the multimodal instrument. The reference output signal may, for example, involve a ballistocardiogram scale, PPG signal from a smart watch or toe PPG sensor, wired or wirelessly coupled to the multimodal instrument and/or to the interface. For instance, where a local computer or handheld device (e.g., mobile telephone) is implemented as the interface, the multimodal and separate remote instruments can be separately coupled to the local computer or handheld device in a time-synchronous manner such that complex measurements can be made.

In some embodiments, the interface directs placement of the multimodal instrument using one or more of a variety of approaches. For instance, remote audio/visual guidance from a health care provider or software entity (e.g., at a remote network node or network cloud-based location) may be communicated to a user, or may be implemented to automatically control operation or placement of the multimodal instrument. Visual cueing can be used for placement of the device on the body, such as by using a local camera for capturing a body image, software, human placement of a "target" marker, or a user/patient's hand being guided to a desired location. Three-dimensional (3D) vision methods can be used to locate an instrument on the user's body, and may employ structured light, multiple cameras and other approaches to do so.

Another example embodiment is directed to an apparatus including a multimodal instrument and a local interface circuit. The apparatus may, for example, be implemented with one or more methods as discussed above. In some embodiments, the multimodal instrument is configured for placement against the body of a user, and captures different types of physiological signals from the user (e.g., using two or more sensors). Each type of physiological signal is captured during operation in one of the respective modes, each mode corresponding to at least one of a plurality of physiological characteristics (e.g., with each mode capturing one or more signals, which are carried out in parallel in certain implementations). The local interface circuit and the multimodal instrument operate in one of the modes for capturing at least one of the different types of physiological signals, and for collecting and recording data corresponding to at least one of the physiological characteristics of the user (corresponding to one of the modes). For instance, two more sensors in the multimodal instrument may be operated in a particular mode, for concurrently detecting different characteristics.

Signals that may be captured for a particular mode may correspond to one or more of ECG signals, impedance plethysmogram (IPG) signals, photoplethysmogram (PPG) signals, optical spectroscopy signals, photographic images, accelerometric signals, phonocardiogram (PCG) signals, heart sounds, electroencephalogram (EEG) signals, piezoelectric signals, electrochemical signals, chemical composition, olfactory characteristics (e.g., via olfactory sensors), resonance, acoustics, chemical characteristics, molecular characteristics and temperature. In some implementations, sensing in the respective modes for capturing such signals may be implemented using two or more types of sensing protocols as implemented in the local interface and/or multimodal instrument. The protocols may, for instance, be implemented via an algorithm.

In some implementations, the interface circuit transmits data characterizing the collected data over a communications network for remote analysis. For instance, different types of physiological signals can be recorded from the instrument (e.g., in parallel). The interface circuit operates with the multimodal instrument to mathematically construct a signal characterizing a physiological characteristic based on the different types of recorded physiological signals, and transmits the constructed signal via the communications network.

In some embodiments, the apparatus includes a separate remote instrument for placement against the body of the user, for providing a reference output. The local interface circuit operates the separate remote instrument and the multimodal instrument to detect physiological characteristics, using the remote instrument as a reference signal that is relative to a signal or signals received from the multimodal instrument. The separate remote instrument may be integrated with, detachable from, wired to, or separate from the multimodal instrument. In a particular implementation, the remote instrument includes a ballistocardiogram scale as discussed above which the user/patient can stand on for obtaining BCG measurements. In another implementation, the remote instrument includes a smart watch with physiologic sensors (e.g., PPG).

Information gleaned via the local interface circuit and multimodal instrument is provided in a variety of manners, to suit particular applications. In some embodiments, the apparatus (e.g., implemented as a system) includes a remote interface circuit that operates with the local interface circuit to transmit data characterizing the operation of the multimodal instrument in the respective modes, and selects one of the modes for use in capturing data corresponding to the at least one of the physiological characteristics. For instance, a medical services provider can remotely control the operation of the multimodal instrument for operating in different modes to capture physiological information from the user. Further, the remote interface can be used to provide instructions to the user for positioning and/or manipulating the multimodal instrument.

In a more particular implementation, the local interface determines a preliminary diagnosis of the user based on the collected data, using an algorithm associated with a mode and/or a physiological characteristic of the user. Data characterizing the preliminary diagnosis (including healthy status) can be provided directly to the user, transmitted over the communications network to a medical service provider, or both. In some implementations, the local interface circuit automatically communicates an instruction to the user, such as to instruct the user to seek medical care, or automatically alerts local medical personnel.

Various other embodiments are shown in the Appendix of the Provisional, which forms part of this patent document. For instance, a multimodal instrument as described herein may be implemented with sensors as shown in the Appendix of the Provisional, with the sensor being manipulated to capture signals such as to focus on capturing the S-T segment of the cardiac cycle. The multimodal instrument may be placed in a different position to capture ECG signals, to align sensors therein with a vector form that can be mathematically manipulated to yield the best ECG waveform to represent the S-T segment and any changes thereto. Further, a palm-based or other remote instrument can be implemented as a reference/ground-type signal for use with cardiac (or other) signals obtained via the multimodal instrument.

In other specific embodiments, the physical examination instrument produces other physiological data relevant to the user cardiac condition. For example, this is applied to collected data concerning the Q and T features of the ECG. The Q-T interval (the time between the Q and T features of the ECG) is one such important cardiac feature to measure. The Q-T intervals are longer for some patients than others, and certain well-known drugs can elongate the interval, and that can in turn lead to fatal arrhythmias By using the physical examination instrument to measure this feature, the care provider can diagnose and treat this condition before the condition becomes fatal.

Turning now to the figures, FIG. 1 shows a block diagram of an exemplary remote examination instrument apparatus 100, in accordance with one or more example embodiments. The examination instrument apparatus 100 is shown with a multimodal instrument 110, a local interface 120 and a remote interface 130. These components may, for example, be implemented as part of a system, together, separately or in combinations thereof as implemented for various embodiments. In some embodiments, the multimodal instrument 110 includes a memory/buffer 116, which is used to buffer or store data when there is no real-time connection to transmit data at a reasonable rate to a remote site.

The multimodal instrument 110 includes one or more sensors, with sensor 112 labeled by way of example, each of which operate to detect a particular physiological characteristic. The respective sensors as shown may, for example, be implemented with separate sensor circuits, processing blocks (e.g., specific circuitry and related processing instructions), or a combination thereof. For instance, where two or more such sensors are employed, a first sensor may be implemented for capturing electrical signals corresponding to cardiac operation, and a second sensor may be implemented for capturing audio for audio-related physiological characteristics. These sensors may be implemented, for example, in accordance with the various embodiments herein.

The multimodal instrument 110 also includes sensor processing circuitry 114 that operates for capturing signals from the respective sensors, and for communicating with the local interface 120 for presenting the captured signals thereto. In certain embodiments, the sensor processing circuitry 114 also configures operation of the sensors in accordance with one or more sensing schemes. In further embodiments, the sensor processing circuitry 114 operates to process signals received from the sensors and perform diagnostic type functions, and communicates with a user of the instrument and/or with the local interface 120 based upon the diagnostics.

In some embodiments, passive sensors that record energy from the physiologic signals themselves (e.g., ECG, acoustic) are utilized. In other embodiments, active sensors inject energy (e.g., light or electrical signals) and measure the body's response (e.g., PPG or ICG, respectively).

In still other embodiments, the multimodal instrument 110 has interactive circuitry for interacting with a user of the multimodal instrument, and the sensor processing circuitry 114 operates the interactive circuitry. For instance, visible, audible or tactile communications can be effected as discussed herein, to alert the user of a placement of the multimodal instrument 110 (e.g., correct or incorrect) or of a physiological condition.

The local interface 120 includes sensor controller circuitry 122 and signal processing circuitry 124. The sensor controller circuitry 122 controls the multimodal instrument 110 using one or more approaches as described herein. For instance, the controller may send configuration data to the multimodal instrument 110, which configures it according to the configuration data. The signal processing circuitry 124 processes one or more physiological signals received from the multimodal instrument 110, and uses the processed signals locally and/or sends the processed signals to the remote interface 130. The signals may be received, for example, via wired or wireless communication links, that may be implemented locally to the multimodal instrument 110. Accordingly, the local interface 120 may be implemented using one or more of a variety of devices, such as a laptop, tablet, handheld device such as a mobile phone, or a dedicated device operable with the multimodal instrument 110 or a display on the multimodal instrument itself, or a projector that projects relevant information onto a surface such as a wall once aligned to do so.

The remote interface 130 operates to receive data output from the local interface 120, such as by communicating via one or more of a variety of networks and network links. In some implementations, the remote interface 130 provides a monitoring input to the local interface 120, such as for configuring or controlling the multimodal instrument 110 or the local interface 120, or for providing instructions to a user of the multimodal instrument 110 as described herein. In certain implementations, the remote interface 130 operates with the local interface 120 to obtain visual feedback indicating a position of the multimodal instrument 110 relative to a user, and provides monitoring input by directing the user to move the multimodal instrument.

Figure 2:
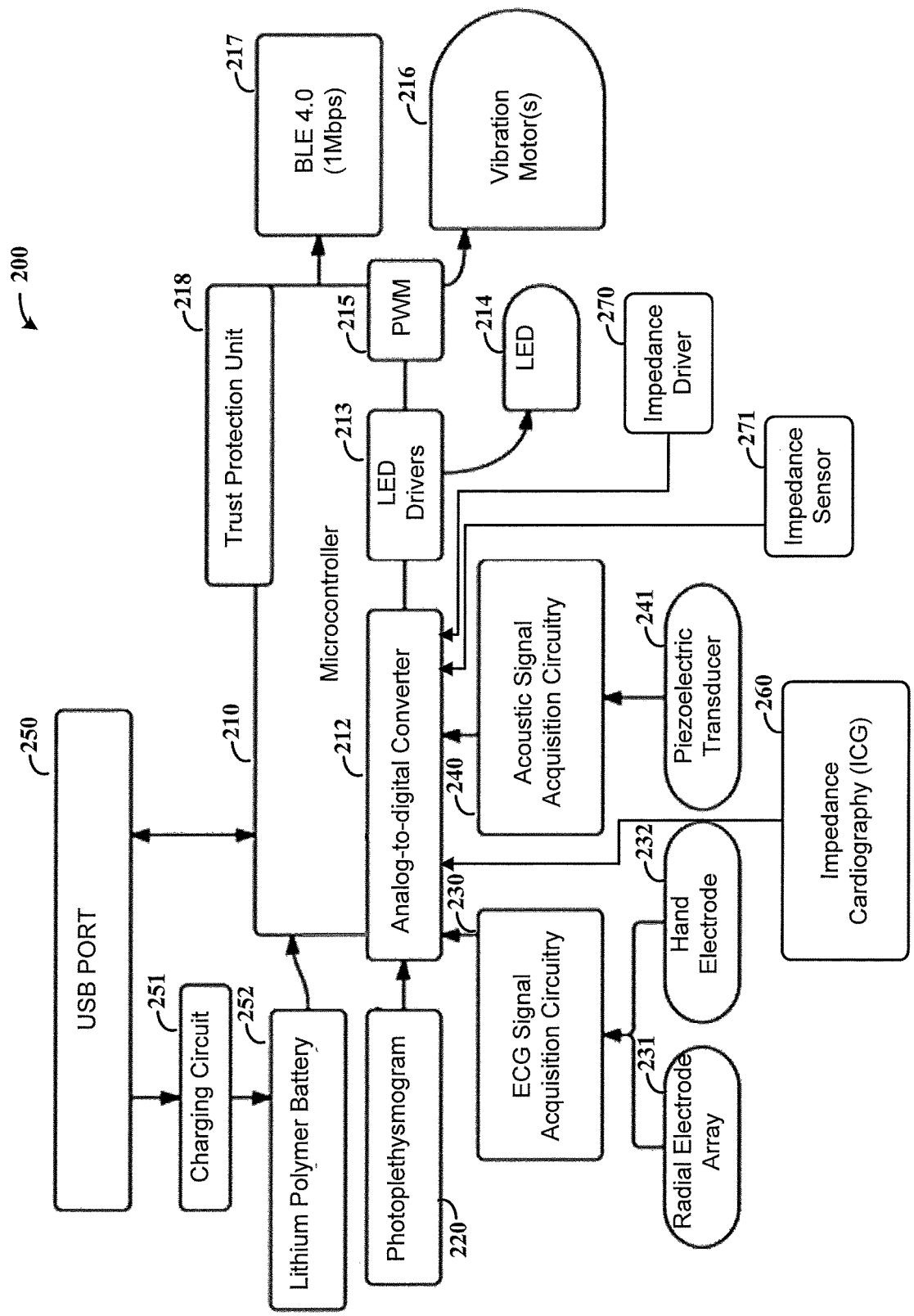
FIG. 2 shows a multimodal instrument, consistent with various aspects of the present disclosure.

FIG. 2 shows a multimodal instrument 200 as may be implemented with a multimodal instrument as described herein, in accordance with one or more example embodiments. The multimodal instrument 200 includes microcontroller 210. In some implementations, the instrument 200 includes multiple input channels, each with appropriate signal-conditioning circuitry, such as one or more operational amplifiers (not shown) for each channel, filters, a multiplexer for time-sharing the A/D, analog-to-digital converter 212, LED drivers 213, pulse-width modulator (PWM) 215, and trust protection unit 218. The LED drivers 213 are shown, by way of example, as operating LED 214, and the PWM circuit 215 is shown, by way of example, as operating vibration motor(s) 216. The multimodal instrument 200 also includes various sensor circuits that include, by way of example, PPG circuit 220, ECG signal acquisition circuitry 230 coupled to a radial electrode array 231 and hand electrode 232, acoustic signal acquisition circuitry 240 along with a piezoelectric transducer 241, and an impedance cardiography (ICG) circuit 260. A USB port 250 is connected to a charging circuit 251 and lithium polymer battery 252 for providing power to the multimodal instrument 200, and for providing communications to the microcontroller 210. Impedance driver 270 and impedance sensor 271 may also be included as part of the instrument.

Figure 3:
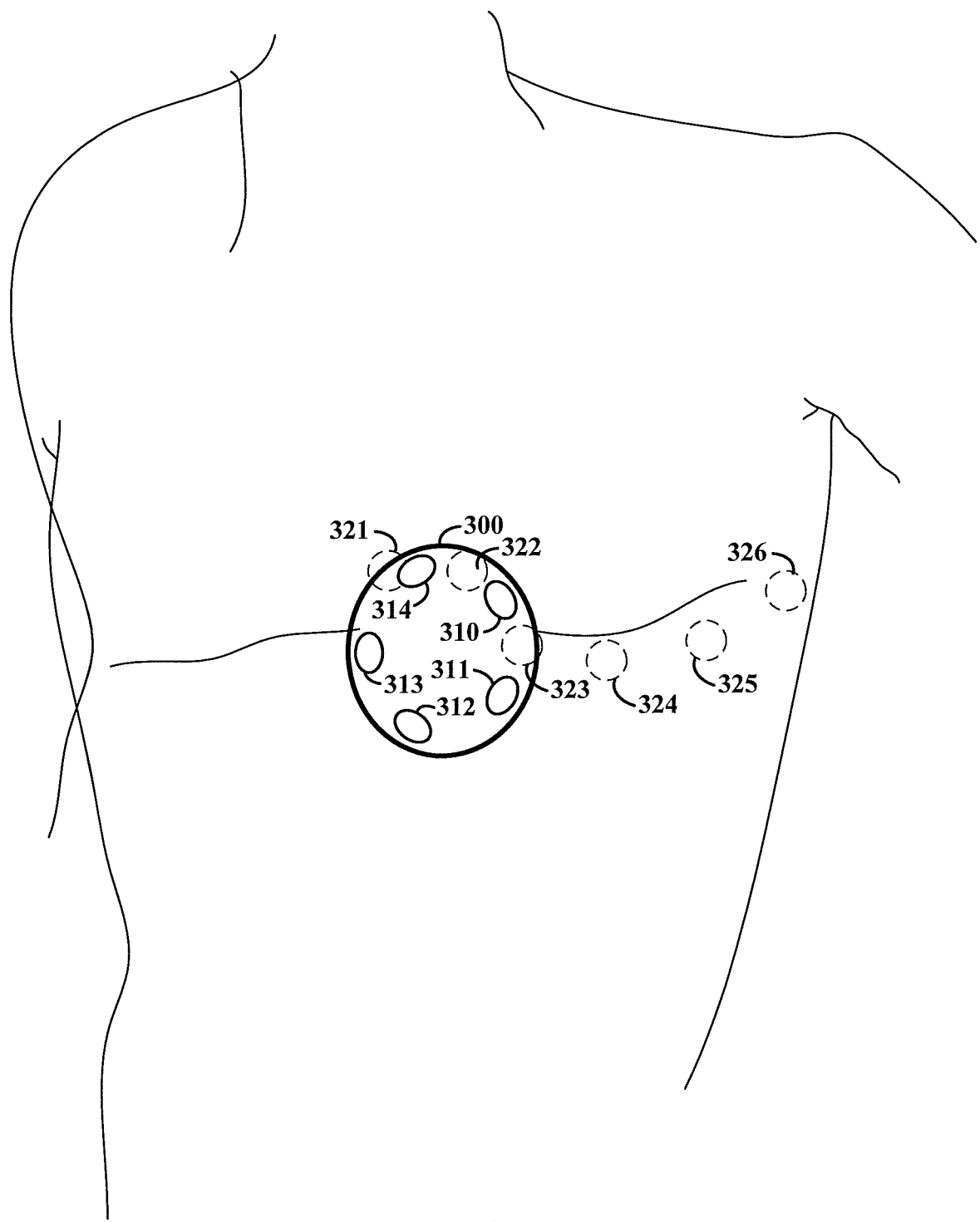
FIG. 3 shows an apparatus as applied for sensing characteristics from a human thorax, consistent with various aspects of the present disclosure.

FIG. 3 shows an apparatus 300 as applied (via a chest strap) for sensing characteristics from a human thorax, in accordance with another example embodiment. The apparatus 300 includes electrodes 310-314 (by way of example), one or more of which may be an additional physiological characteristic sensor such as an acoustic sensor. The apparatus 300 can be rotated or otherwise positioned to collect data from different regions of the thorax, such as via ECG-type sensing regions 321-326. For instance, rotation can be directed as discussed herein such that the user (or patient) can manipulate the apparatus 300 to obtain different signals that can be used to construct an ECG. Viewing such rotation in the context of a hexaxial reference system situated relative to the cardiac axis (e.g., +60 degrees), the user or patient can direct (e.g., by using his or her hand) manipulation of the apparatus to specific angles for locating the positions of the leads or electrodes (see FIGS. 4A and 4B herein and diagrams on page 1 of the Provisional Appendix). The apparatus can also be used to concurrently detect other characteristics, such as acoustic characteristics as may be similar to those collected via a stethoscope. The detected signals can be combined and used to provide an indication of a cardiac condition of the user.

In some implementations, ECG-type signals are mathematically processed to generate an output signal representative of a different (e.g., standard, or partial such as ST-segment or QT-interval) ECG signal, as may be obtained via ECG electrodes at different locations on the thorax and/or via additional electrodes. For instance, variations in heart rate over time (e.g., due to breathing or relaxing) can be accounted for, and positioning of the apparatus 300 (e.g., as sensed via orientation sensors), can be used in generating the output signal. In some implementations, the apparatus 300 is moved to different locations on the thorax and used to obtain different signals, which can be combined.

Figure 4A:
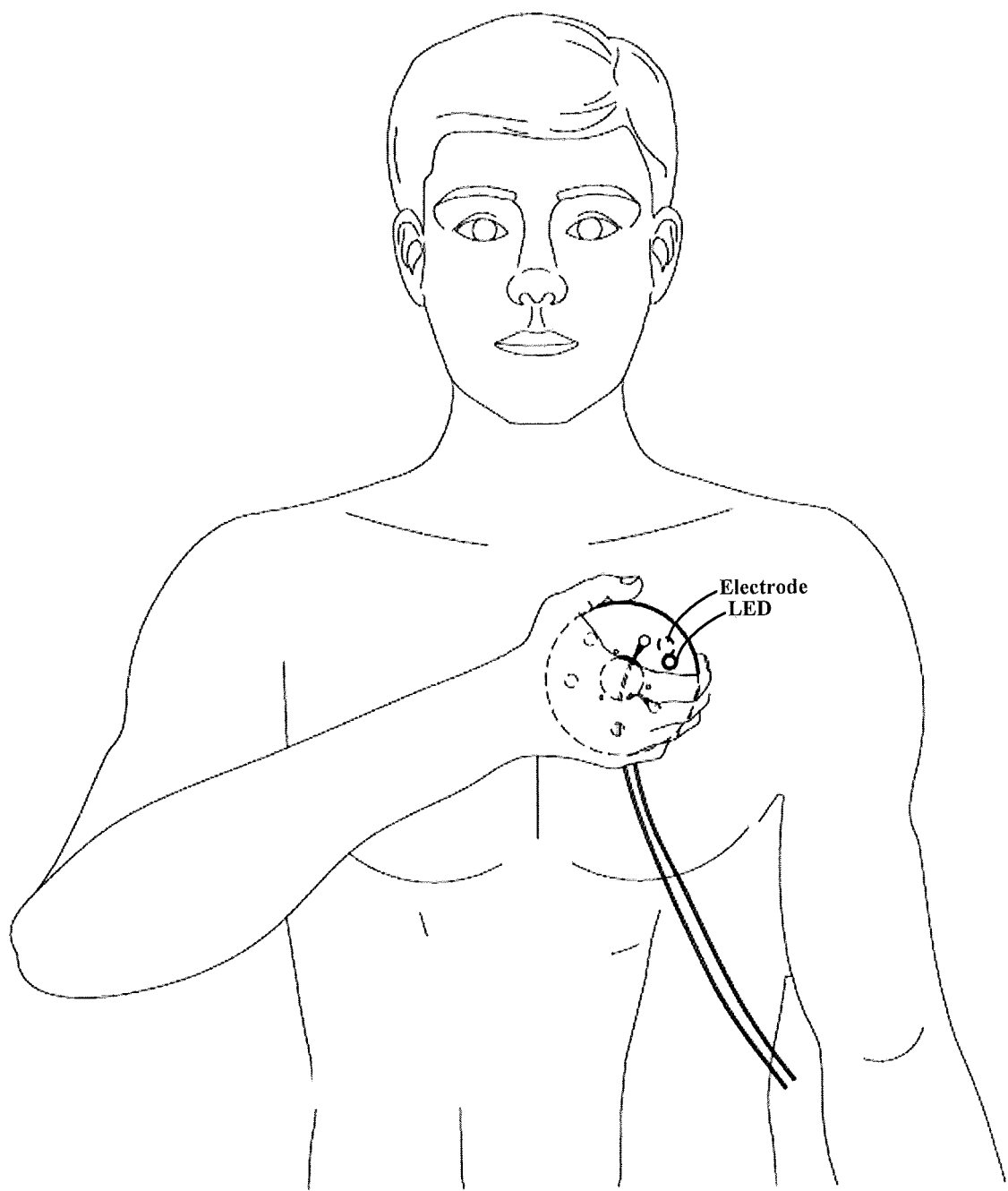
FIGS. 4A-4B show an example of an apparatus as rotated or positioned to collect data from different regions of a human thorax, in accordance various embodiments.
Figure 4B:
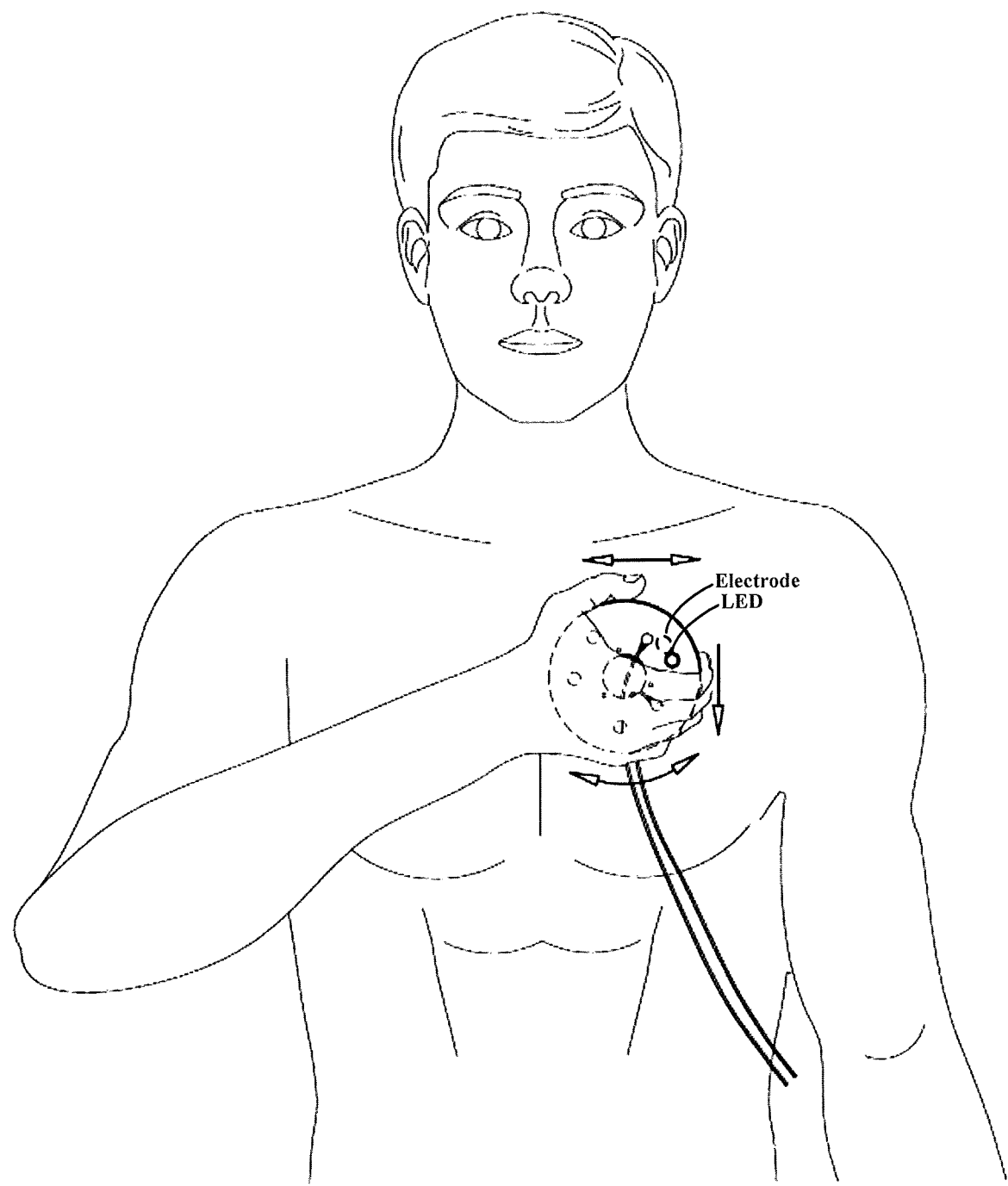

FIGS. 4A-4B show an example of an apparatus as rotated or positioned to different locations for collecting data from different regions of a human thorax, in accordance various embodiments. The apparatus illustrated by FIGS. 4A-4B can include the apparatus 300 illustrated and previously described by FIG. 3. As described above, the apparatus can be rotated or otherwise positioned by the user to collect data from different regions of the thorax, such as via electrodes and/or ECG-type sensing regions (e.g., ECG-type sensing regions 321-326 and the electrodes 310-314 as illustrated by FIG. 3). By using his or her hand, the user can position the apparatus to obtain different signals that can be used to construct an ECG, such as rotating or positioning the apparatus at specific angles for locating the positions of the leads or electrodes. In specific embodiments, the user can be directed by guidance and/or feedback to translate and/or rotate the apparatus. Although the embodiments of FIG. 4A-4B illustrates one labelled electrode in the figures (and respectively one labelled LED), the apparatus includes a plurality of electrodes (similar and/or identical to the illustration of FIG. 3) that are located on a side of the apparatus that is proximal to the user's body (e.g., the user's chest), which may be referred to as a "body-contacting surface" of the apparatus. Similarly, the apparatus can include a plurality of LEDs that are located on the opposite side of the apparatus from the electrodes, which may be proximal to the user's hand.

As a specific example, FIG. 4A illustrates an apparatus positioned by the user at a first location. The user may move the apparatus from the first location to a second or more locations. Such movement can include moving the apparatus toward their head (e.g., up), toward their feet (e.g., down), toward their left arm, and/or toward their or right arm (e.g., left or right). The user may, alternatively and/or in addition, adjust the position of the apparatus by rotating the apparatus radially (e.g., rotating the apparatus a specific angle or degree). FIG. 4B illustrates the apparatus illustrated by FIG. 4A that is located at an example second location.

In specific embodiments, the user can be provided guidance and/or feedback for placement of the multimodal instrument through the use of video, audio, optical, and/or tactile cues. For example, a user is guided, remotely by a health care provider (e.g., doctor, nurse, or software entity), through a remote cardiology examination. As illustrated by FIGS. 4A-4B, the cue can be provided by mounting optical beacon(s) (e.g., LEDs) on the top cover or rim of the sensor on the exterior of the instrument (e.g., on the opposite side of the instrument from the electrodes). The pulsating or steady light emitted from the beacons can be received and processed by a camera/light sensor circuit a short distance from the user and communicated to the remote examination computer to determine current positioning of the sensor relative to the user and to determine any corrective measures needed to reposition the sensor to the proper location on the patient for optimal sensor measurements. Although embodiments are not so limited, and the feedback and/or guidance can be provided in a variety of ways, as previously described herein.

The apparatus, as previously described, can be in communication with a reference device via a wired or wireless link (e.g., as illustrated by the arrow). The reference is sometimes herein referred to as a reference instrument. Example reference devices can include a scale, a smartphone, a wearable (e.g., wristwatch or other wearable device), a tablet, etc. As previously described, the reference device (e.g., reference instrument) can be placed against the body of the user and used Lo provide a reference output signal that can be used by the local interface circuit, relative to one or more signals obtained by the multimodal instrument. The reference output signal may, for example, involve a ballistocardiogram scale, PPG signal from a smart watch or toe PPG sensor, wired or wirelessly coupled to the multimodal instrument and/or to the interface. For instance, where a local computer or handheld device (e.g., mobile telephone) is implemented as the interface, the multimodal and separate remote instruments can be separately coupled to the local computer or handheld device in a time-synchronous manner such that complex measurements can be made.

Various blocks, modules or other circuits may be implemented to carry out one or more of the operations and activities described herein and/or shown in the appended figures. In these contexts, a "block" (also sometimes "circuitry," "module," or mixed-signal circuitry with both analog and digital circuitry) is a circuit that carries out one or more of these or related operations/activities (e.g., coupling a sensor signal, coupling multiple sensors, or processing one or more outputs from a sensor or sensors). For example, in certain of the embodiments herein, one or more modules are discrete circuits and/or programmable logic circuits configured and arranged for implementing these operations/activities, as in circuit modules coupled to sensors as shown in the figures. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer programmable product (e.g., nonvolatile memory device), which includes a machine or computer-readable medium having stored thereon instructions which may be executed by a computer (or other electronic device) to perform these operations/activities. Some implementations are directed to a computer programmable product (e.g., including nonvolatile memory for storing executable code), which may be executed by an embedded CPU (or other electronic device) to perform such operations/activities. These approaches may be implemented, for example, to facilitate use of a multimodal instrument as described herein for bulk manufacture, with individual feature sets and algorithms (e.g., for specific disease states) being specified prior to implementation by programming the nonvolatile memory.

In more detailed/experimental embodiments of the present disclosure, an examination system includes a remote physical examination instrument, optionally a camera (or mirror) that faces a user during his or her examination, processor circuitry (e.g., a computer for processing the data collected in the examination), and a monitor or display. The remote physical examination instrument is implemented in the form of a hand-fitting glove, with a circular array of electrodes around an exterior of the glove's palm (and/or fingertips) to contact a chest of the user and an electrode within the glove that contacts a palm of the user. The processor circuitry may be entirely contained on the back of the glove, or limited communication circuitry may be implemented on the glove to permit transmission of the electrode signals (via wired or wireless communication) to remote processing circuitry. The signal data from the electrodes may be transmitted to a remote device or CPU for display/analysis, (further) processing, and data storage.

In various experimental embodiments of the present disclosure, a remote physical examination instrument may be activated by motion detected by a sensor (e.g., accelerometer, proximity sensor, etc.) or by manual activation. In more specific embodiments, where the remote physical examination instrument is a glove, manipulation of a joint in the hand or wrist may activate the instrument, and/or a microphone or other detection device may activate the instrument in response to visual, audible, or other sensory queues.

In further experimental embodiments, where the remote physical examination instrument is a glove, the back-side of the glove is outfitted with one or more LEDs to provide information to a camera and image processing system including position, relative position of fingers, tilt and rotation of the glove relative to the chest of the user. A monitor displays an image of the patient, obtained using the camera. A marker, such as a blinking red dot, may indicate the desired position of the glove relative to the actual location of the glove. Once appropriately positioned, one or more sensory queues are provided to the user (e.g., vibration of the glove, via the monitor, etc.). Further examinations or multiple measurements for an examination are completed by a similar methodology in various embodiments, involving location selection and patient relocation of the sensor.

Further aspects of the present disclosure are directed to selecting optimal electrodes on the glove for a selected physical examination or mode of examination. For example, for an ECG examination, electrodes are to be selected from electrodes on the exterior palm of the glove based in part on the location and orientation of the glove provided to the camera via the LEDs provided on the back-side of the glove, and interpreted by processing circuitry. ECG measurements could also be made relative to an additional electrode on a sensor within the glove that contacts a finger or palm of the patient's hand, allowing for a "limb" lead (a clip-on device to one of the user's digits) used as a reference for the ECG (relative to any of the plurality of sensors on the exterior palm of the glove). Alternatively, electrodes on the sensor can be provided to touch the thumb and index finger, for example, for a "pinch" grip. In such configurations, multiple electrodes can be used to measure the local tissue impedance variations or optical variations via a PPG with each pulse, providing another method of measuring heart rate or pulse arrival time (PAT). From the PAT measurement, pulse wave velocity can be estimated, as well as blood pressure.

According to other aspects, the present disclosure is directed to processing electrode data at a location remote from the location of physical instrument (e.g., where a patient is examined with the instrument). In such embodiments processing of the electrode data may include decimation, filtering, fusion (combination to create derivative information), denoising, synthesis of standard ECG leads, or other analysis. In various embodiments, this processing is performed at one or more locations, including: processing circuitry in the remote instrument, a portable computing device, a local interface (e.g., smart phone, tablet, laptop, desktop PC, or any other computer processing device), a remote computer at a specific location (e.g., doctor's office) or in the cloud (remotely over a communication network). As various combinations of data processing can occur at various remote and user locations permit, related implementations embrace a spectrum of combinations, ranging at one end in which all such processing is done within circuitry built into the handheld device, covering applications with processing circuitry in proximity to and working in response to raw data from the handheld device, and also covering applications in which raw data is sent from the handheld device for processing by remotely-located circuitry (whether located at a doctor's examination office or another medical-data interpretation facility where such raw data is assessed). In yet further embodiments, the electrodes can simultaneously detect data relevant to various physical examinations.

For example, simultaneous capture of synchronized ECG and heart sound information, allowing for detailed timings, valve functions, etc.

In yet other experimental embodiment of the present disclosure, the remote physical examination instrument may communicate and access information from a pacemaker (e.g., defibrillator or other implantable device). For example, where the medical device is internally implanted within the user (e.g., pacemaker), the remote physical examination instrument may further include one or more (short-range) wireless communications transceivers. Data is then securely communicated by the medical device to the remote physical examination instrument where the data may be processed/analyzed, similar to the electrode data, to assist in determining a condition of the user. In another specific embodiment, interface circuitry is included with the cardia/lung device which dumps its sensed and stored data to the local interface circuit (e.g., on-site handheld device or other locally-situated computer/device) and thus onward to the care provider. In specific pacemaker-directed embodiments in which the pacemaker requires a magnet to be held over the pacemaker (to enable/activate communications), the physical examination instrument and the local interface circuit are respectively configured with wireless communication circuitry (typically including an antenna in the physical examination instrument and a receiving coil in the local interface circuit).

Based upon the above discussion and illustrations, those skilled in the art will readily recognize that various modifications and changes may be made to the various embodiments without strictly following the exemplary embodiments and applications illustrated and described herein. For example, a variety of different sensing instruments may be used on the remote physical examination instrument and/or may be combined to allow the remote physical examination instrument to sense for a plurality of physical conditions of a patient. In addition, the various embodiments described herein may be combined in certain embodiments, and various aspects of individual embodiments may be implemented as separate embodiments. Such modifications do not depart from the true spirit and scope of various aspects of the invention, including aspects set forth in the claims.

What is claimed is:

1. An apparatus comprising:
   a multimodal instrument including a radial array of electrodes arranged around a perimeter of a body-contacting surface of the instrument, the body-contacting surface including the radial array of electrodes configured to be placed against a chest of a user, and to capture a plurality of different types of physiological signals from the user while the radial array of electrodes are in contact with the chest of the user, each type of physiological signal being captured during operation in one of respective modes, each mode corresponding to at least one of a plurality of physiological characteristics; and
   a local interface circuit configured and arranged with the multimodal instrument to:
   operate the multimodal instrument in one of the modes for capturing at least one of the plurality of different types of physiological signals,
   collect and record data corresponding to at least one of the plurality of physiological characteristics of the user corresponding to the one of the modes, and
   transmit data characterizing the collected data via a wired or wireless link.

2. The apparatus of claim 1, wherein the multimodal instrument is circular shaped and the radial array of electrodes includes a circular array of electrodes arranged around a circular perimeter of the body-contacting surface of the multimodal instrument, and the local interface circuit is further configured and arranged to select electrodes from the radial array for collecting data from or for using the collected data from the selected electrodes.

3. The apparatus of claim 1, wherein:
the multimodal instrument being shaped for the user to grasp in one hand and place against the chest of the user while grasped in the one hand, and at least one separate electrode upon a separate surface thereof configured and arranged for contacting the one hand of the user during application of the multimodal instrument to the chest of the user via the user's hand, and
the multimodal instrument is configured and arranged with the local interface circuit to derive electrocardiogram (ECG) signals using one or more of the electrodes of the radial array and one or more of the at least one separate electrode arranged for contacting the user's hand and for moving the multimodal instrument to different locations or rotating the radial array of electrodes while collecting signals from the one or more electrodes of the radial array of electrodes.

4. The apparatus of claim 1, further including a remote interface circuit that is remotely located from the multimodal instrument,
the local interface circuit being configured and arranged to transmit the collected data via another wireless link to the remote interface circuit; and
the remote interface circuit being configured and arranged to process the collected data based on an algorithm associated with the at least one of the physiological characteristics and to reconstruct signals corresponding to lead signals, the processed collected data being indicative of a diagnosis of the user, and the remote interface circuit including circuitry selected from the group consisting of: a smartphone, a tablet, a set-top box, a gaming console, a computer, and circuitry accessed using a cloud system.

5. The apparatus of claim 1, wherein the local interface circuit is further configured and arranged to provide guidance to the user, the guidance being indicative of feedback selected from the group consisting of: a position of the multimodal instrument, taking breaths, holding breath, exhaling, coughing, Valsalva maneuver, and a combination thereof.

6. The apparatus of claim 1, wherein:
the multimodal instrument includes at least two sensors respectively configured and arranged to sense different types of characteristics of the user, and
the local interface circuit is configured and arranged to control the multimodal instrument for selectively operating at least one of the at least two sensors based on a selected one of the modes.

7. The apparatus of claim 6, wherein the multimodal instrument includes respective sensors configured and arranged to sense at least two of: electrical characteristics, optical characteristics, acoustical characteristics, chemical characteristics and mechanical characteristics and the local interface circuit is configured and arranged with the multimodal instrument to operate the multimodal instrument in one of the modes further includes:
sequentially capturing a signal from each of the electrodes of the array and comparing the each captured signal to a reference.

8. The apparatus of claim 6, wherein the multimodal instrument includes respective sensors configured and arranged to sense characteristics that correspond to at least two of: electrocardiogram (ECG) signals, impedance plethysmogram (IPG) signals, photoplethysmogram (PPG) signals, optical spectroscopy signals, photographic images, accelerometric signals, phonocardiogram (PCG) signals, heart sounds, electroencephalogram (EEG) signals, piezoelectric signals, electrochemical signals, chemical composition, olfactory characteristics, resonance, acoustics, chemical characteristics, molecular characteristics, and temperature.

9. The apparatus of claim 1, wherein:
the multimodal instrument includes a plurality of electrodes around the perimeter of the body-contacting surface of the multimodal instrument in the radial array, and at least one separate electrode upon a separate surface thereof configured and arranged for contacting a user's hand during application of the multimodal instrument to the user's chest via the user's hand, and
the multimodal instrument is configured and arranged with the local interface circuit to provide electrocardiogram (ECG) signals by selecting different ones of the plurality of electrodes arranged radially around the body-contacting surface of the multimodal instrument, deriving ECG signals from one or more of the plurality of electrodes around the body-contacting surface relative to each other, or the plurality of electrodes around the body-contact surface relative to one or more of the at least one separate electrode.

10. The apparatus of claim 9, wherein the multimodal instrument includes position sensors configured and arranged to:
detect a position of the instrument relative to the user based upon at least one of a magnetic sensor relative to the Earth's gravitational and/or magnetic fields, and cardiac signals measured relative to each other,
capture cardiac electrical signals from the user, and
mathematically transform the captured cardiac electrical signals to signals of standard ECG leads that are different from a position of the instrument.

11. The apparatus of claim 1, further including a separate remote instrument configured and arranged to be placed against the body of the user and to provide a reference output, wherein the local interface circuit coupled by a wired or wireless connection to the remote instrument and the multimodal instrument to detect the physiological characteristics using the separate remote instrument as a reference signal, relative to a signal received from the multimodal instrument, and
the local interface circuit is configured and arranged with the multimodal instrument to operate the multimodal instrument in the one of the modes includes sequentially capturing a signal from each of the electrodes of the array and comparing the each of the captured signals to the reference signal to collect the data.

12. The apparatus of claim 11, wherein the separate remote instrument includes at least one of: a ballistocardiogram scale and a wrist-worn photoplethysmogram sensor.

13. The apparatus of claim 11, wherein the separate remote instrument is coupled via wired or wireless connection with the multimodal instrument in a handheld sensor device and is configured and arranged to sense characteristics from the user's hand or hands.

14. The apparatus of claim 1, wherein the local interface circuit is configured and arranged with the multimodal instrument to record different physiological signals from sensors of the multimodal instrument in parallel, mathematically construct a signal characterizing a physiological characteristic based on the different recorded physiological signals and which conforms to a signal collected from the user via sensors placed on the user in locations that are different than the locations at which the sensors of the instrument are actually placed, and transmit the constructed signal via the wired or wireless link to the local interface circuit.

15. The apparatus of claim 1, wherein the local interface circuit is configured and arranged to:
   operate the multimodal instrument in the one of the modes including sequentially capturing a first signal from a first electrode of the array simultaneously with a second signal from a second electrode of the array and comparing the first signal and the second signal to collect the data;
   determine a preliminary diagnosis of the user based on the collected data, using an algorithm associated with the at least one of the physiological characteristics, and
   transmit data characterizing the preliminary diagnosis via the wired or wireless link.

16. The apparatus of claim 1, wherein the local interface circuit is configured and arranged to operate the instrument in at least one of the modes for capturing a plurality of the different types of physiological signals, and to determine a preliminary diagnosis of the user based on the plurality of different types of the physiological characteristics.

17. The apparatus of claim 1, wherein:
   at least one of multimodal instrument and the local interface circuit further includes a camera configured and arranged to capture an image of the user that is indicative of a placement of the multimodal instrument and communicate the image of the user to the local interface circuit; and
   the local interface circuit being further configured and arranged to provide feedback to the user for guiding placement of the multimodal instrument via a visual display of the image of the user, guidance for the placement of the multimodal instrument being determined based on at least one data selected from the group consisting of: light emitting diode (LED) beacons emitted by LEDs on a surface of the multimodal instrument and as captured by the camera, signals from an inertial measurement unit or magnetic sensor arranged on the multimodal instrument, a quality of one or more of the physiological signals captured by the multimodal instrument, and a combination thereof.

18. The apparatus of claim 17, wherein the feedback includes a displayed image of the user and an indication of successful positioning of the instrument, the indication including at least one of a change of color blinking on a marker of the image of the user, an audible tone, and a vibration from the instrument.

19. The apparatus of claim 1, wherein:
   the multimodal instrument further includes optical beacons configured and arranged to emit light as a visual guidance for placement of the multimodal instrument on the user's body;
   at least one of multimodal instrument and the local interface circuit further includes a camera configured and arranged to capture and communicate the emitted light to the local interface circuit, and
   the local interface circuit being configured and arranged to determine a current position of the multimodal instrument and provide position feedback to the user to reposition the multimodal instrument.

20. The apparatus of claim 1, wherein the multimodal instrument further includes an inertial measurement unit or magnetic sensor configured and arranged with the local interface circuit to determine an orientation of the multimodal instrument and to provide position feedback to the user.

21. The apparatus of claim 1, wherein the multimodal instrument further includes a memory circuit configured and arranged to buffer or store data responsive to a connection for transmitting data via the wired or wireless link being outside a threshold rate.

22. A method comprising:
   placing a multimodal instrument, having a radial array of electrodes arranged about a perimeter of a body-contacting surface of the instrument, the body-contacting surface including an array of electrodes, against a chest of a user and using the multimodal instrument to capture a plurality of different types of physiological signals from the user while the radial array of electrodes are in contact with the chest of the user, each type of physiological signal being captured during operation in one of respective modes, each mode corresponding to at least one of a plurality of physiological characteristics; and
   using a local interface circuit and the multimodal instrument to:
      operate the multimodal instrument in one of the modes for capturing at least one of the plurality of different types of physiological signals,
      collect and record data corresponding to at least one of the plurality of physiological characteristics of the user corresponding to the one of the modes, and
      transmit data characterizing the collected data for processing locally or remotely via a wired or wireless link.

23. The method of claim 22, further including providing feedback for placement of the multimodal instrument to the user including at least one of: displaying an image of the user and a visual indication of successful positioning of the instrument on a display of the local interface circuit, changing a color of a blinking light on the multimodal instrument and/or on the image of the user, providing an audible tone, providing a vibration from the instrument, and a combination thereof, and wherein the multimodal instrument is handheld and the feedback for placement is indicative of rotating the radial array or changing a position of the radial array.

24. The method of claim 22, further including using structured lights or multiple cameras to determine a location of the multimodal instrument on the user's chest via three-dimensional vision techniques.

25. The method of claim 22, wherein using the local interface circuit and the multimodal instrument includes recording the plurality of different physiological signals from the multimodal instrument simultaneously or synchronously and using the plurality of different types of physiological signals to extract additional information.

26. The method of claim 22, wherein using the local interface circuit and the multimodal instrument includes simultaneously recording a time-synchronized electrocardiogram and heart sound information and using the electrocardiogram and heart sound information to extract additional information including the relative timing between these signals.

27. The method of claim 22, wherein using the local interface circuit and the multimodal instrument includes recording different physiological signals from the multimodal instrument in parallel, mathematically constructing a signal characterizing a physiological characteristic based on the different recorded physiological signals, and transmitting the constructed signal via the wired or wireless link.

28. The method of claim 22, wherein the multimodal instrument is a handheld instrument and the user places the handheld instrument against the user's chest by grasping the handheld instrument, and wherein placing the multimodal instrument against the chest of the user includes remotely directing an examination of the user by providing instructions to the user regarding placement, via the local interface circuit, the instructions being indicative of a rotation of the radial array.

29. The method of claim 28, further including coupling a signal sensor to the user's hand, and using the local interface circuit with the multimodal instrument and the signal sensor to capture the at least one of the different types of physiological signals at a location at or near the user's hand and to capture at least one other of the plurality of different types of physiological signals at a location at or near the user's chest.

30. The method of claim 22, wherein the multimodal instrument includes at least two sensors respectively configured and arranged to sense different types of characteristics of the user, and wherein using the local interface circuit and the multimodal instrument includes controlling the at least two sensors, via the local interface circuit, for selectively operating at least one of the at least two sensors based on a selected one of the modes.

31. The method of claim 30, wherein using the local interface circuit and the multimodal instrument includes operating the at least two sensors in response to at least two different types of sensing protocols for sensing different physiological characteristics, by storing and executing the sensing protocols in the local interface circuit for controlling the operation of the at least two sensors.

32. The method of claim 22, further including placing a separate remote instrument against the chest of the user and using the separate remote instrument to provide a reference output, wherein using the local interface circuit and the multimodal instrument includes detecting the physiological characteristics using the separate remote instrument to provide a reference signal, relative to a signal received from the multimodal instrument.

33. The method of claim 22, wherein using the multimodal instrument to capture a plurality of different types of physiological signals includes using respective sensors to capture at least two of: electrical characteristics, optical characteristics, acoustic characteristics, chemical characteristics and mechanical characteristics.

34. The method of claim 22, further including processing at least two of the different types of physiological signals together, using the local interface circuit and the multimodal instrument, to provide at least one of a combined parameter and a signal having a lower signal-to-noise characteristic than the at least two of the different types of physiological signals.

35. The method of claim 22, further including providing at least one of a video, audio, and optical feedback to the user using the local interface circuit and the multimodal instrument, the video, audio, and optical feedback including data selected from the group consisting of: video feedback for guiding placement of the multimodal instrument, visual feedback via beacon light emitting diodes changing blink patterns, color, and/or brightness, audio feedback for guiding placement of the multimodal instrument, tactile feedback or audio cues to guide placement of the multimodal instrument, and a combination thereof.

36. The method of claim 35, further including using a remote interface circuit in communication with the local interface circuit to provide the video, audio, and/or optical feedback to the user via input from a health care provider and/or software entity.

* * * * *